(12) United States Patent
Chowdhury

(10) Patent No.: US 6,284,251 B1
(45) Date of Patent: Sep. 4, 2001

(54) BHV-1 GENE-DELETED VIRUS VACCINE

(75) Inventor: Shafiqul I. Chowdhury, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 09/240,173

(22) Filed: Jan. 29, 1999

Related U.S. Application Data (63) Continuation-in-part of application No. 08/607,323, filed on Feb. 26, 1996, now Pat. No. 6,221,360.

(51) Int. Cl.[7] ................ A61K 39/265; A61K 39/295; C12N 7/01; C12Q 1/70
(52) U.S. Cl. ................ 424/199.1; 424/229.1; 435/235.1; 435/236; 435/320.1; 435/5; 435/7.1; 435/7.4
(58) Field of Search .................. 424/199.1, 229.1, 424/205.1; 435/235.1, 234, 5, 7.1, 7.4, 320.1

(56) References Cited

U.S. PATENT DOCUMENTS

| | | |
|---|---|---|
| 4,569,840 | 2/1986 | Kit . |
| 4,703,011 | 10/1987 | Kit et al. . |
| 4,810,634 | 3/1989 | Post et al. . |
| 4,824,667 | 4/1989 | Kit et al. . |
| 5,599,544 * | 2/1997 | Cochran et al. ............ 435/235.1 |
| 5,789,177 * | 8/1998 | Rijsewijk et al. ............ 345/7.1 |
| 5,874,279 * | 2/1999 | Cochren et al. ............ 435/235.1 |

FOREIGN PATENT DOCUMENTS

| | | | |
|---|---|---|---|
| 2057387 | 12/1991 | (CA) | . |
| 668356 * | 8/1995 | (EP) | .......... C12N/15/38 |
| 8910965 | 11/1989 | (WO) | . |
| 9221751 | 12/1992 | (WO) | . |
| 9302104 | 2/1993 | (WO) | . |
| 9400586 | 1/1994 | (WO) | . |
| 8700862 | 2/1998 | (WO) | . |

OTHER PUBLICATIONS

Chowdhury, S. I. Veterinary Microbiolgy 52:13–26, 1996.*
Schrijver et al. Vaccine 15 (17/18):1908–1916, 1997.*

* cited by examiner

*Primary Examiner*—Mary E. Mosher
(74) *Attorney, Agent, or Firm*—Hovey, Williams, Timmons & Collins

(57) ABSTRACT

A safe live recombinant virus as well as a vaccine is produced by the deletion of a portion of the native glycoprotein E (gE) coding region of bovine herpesvirus 1 (BHV-1) followed by the insertion of a plasmid including a foreign functional β-gal at the gE locus. The deletion of gE gene stably attenuates the virus and serves as an immunological marker differentiating vaccinated animals from infected animals. Moreover, production of β-gal allows easy assessment of gEΔ3.1IBRβ virus replication in vaccinated animals and serves as a phenotypic marker which distinguishes it from wild type virus replication in infected animals.

31 Claims, 7 Drawing Sheets

BHV-1 GENE-DELETED VIRUS VACCINE

This application is a continuation in part of application Ser. No. 08/607,323 filed Feb. 26, 1996 now 6,221,310.

BACKGROUND OF THE INVENTION

1. Field of the Invention

The present invention is broadly concerned with recombinant bovine herpesvirus vaccines and corresponding methods. More particularly, the present invention is preferably concerned with the construction of an infectious recombinant bovine herpesvirus type 1 (BHV-1) having deleted portion of the native glycoprotein E (gE) coding region and a functional β-galactosidase gene (β-gal) inserted therein at the gE locus. The deletion of the native gE coding region attenuates the virus and serves as a genotypic or immunological marker which differentiates gE-deleted recombinant virus from wild type virus infection. Additionally, the insertion of the β-gal gene provides for a phenotypic method of assaying for the presence of gE-deleted recombinant virus infection by expressing β-gal activity in host cells.

2. Description of the Prior Art

Bovine herpesvirus type 1 (BHV-1), also known as infectious bovine rhinotracheitis virus (IBRV), is associated with a variety of clinical diseases including rhinotracheitis, conjunctivitis, genital infections, and occasionally abortion, enteritis, encephalitis, and generalized systemic infections in cattle. The genome of BHV-1 consists of a linear dsDNA molecule of about 140 kb. It is composed of a unique long ($U_L$) region and a unique short ($U_S$) region that are flanked by internal and terminal inverted repeat sequences ($I_R$ and $T_R$, respectively). The BHV-1 genome encodes for approximately 70 proteins (Misra et al., Proteins Specified Bovine Herpesvirus 1 (Infectious Bovine Rhinotracheitis, 40 J. Virol. 367–378 (1981)). Like several other animal herpesviruses, the BHV-1 genome encodes for the glycoprotein (g) gE gene. The BHV-1 gE gene sequence, which codes for 575 amino acid (aa) residues, has been reported for two different strains (Leung—Taek, P. et al., The Complete DNA Sequence and the Genetic Organization of the Short Unique Region ($U_S$) of the Bovine Herpesvirus Type 1 Strain (ST strain), 199 Virology 409–421 (1994); Rebordosa, X. et al., Mapping, Cloning and Sequencing of a Glycoprotein—Encoding Gene From Bovine Herpesvirus Type 1 Homologous to the gE Gene From HSV-1, 149 Gene 203–209 (1994)). The predicted gE amino acids contain stretches of hydrophobic amino acids at the N terminus (putative signal sequence) and near the C terminus (transmembrane sequence), which is typical of class 1 integral membrane proteins. The BHV-1 gE, and its homologs in other herpesviruses, have been shown to be dispensable for in vitro replication, but deletion of the entire gE coding sequence of the pseudorabies virus (PRV) genome is responsible for both the reduced virulence of the live vaccine strains Norden and Bartha (Petrovskis, E. A. et al., Deletion in Vaccine Strains of pseudorabies Virus and Their Effect on Synthesis of Glycoprotein gp 63, 60 J. Virol. 1166–1169 (1986) and the alteration of neuroinvasiveness (Card, J. P. et al., Pseudorabies Virus Envelope Glycoprotein gI Influences Both Neurotropism and Virulence During Infection of the Rat Visual System, 66 J. Virol. 3032–3041 (1992)). Thus, expression of the gE gene is required for full pathogenic potential of viruses in animals but is not required for growth in tissue culture (Kritas et al., Invasion and Spread of Single Glycoprotein Deleted Mutants of Aujeszky's Disease Virus (ADV) in the Trigeminal Nervous Pathway of Pigs After Intranasal Inoculation, 50 Vet. Micobiol. 323–334 (1994); Kritas et al., Role of Envelope Glycoproteins gI, gp63 and gIII in the Invasion and Spread of Aujeszky's Disease Virus in the Olfactory Nervous Pathway of the Pig, 75 J. General Virol. 2319–2327 (1994)).

Recently, gE gene-deleted mutants of PRV and IBR have been of interest with respect to their usefulness as differential marker vaccines. Currently, a gE-deleted marker vaccine is being used for the eradication of IBR in Europe. However, this gE-deleted vaccine strain in Europe lacks a β-gal marker which allows for in situ histochemical detection methods for the detection of β-gal enzyme activity and in situ histochemical methods or immunoblotting methods for the detection of β-gal protein. The coding region of β-gal also serves as a genotypic marker of the recombinant virus. The virus can be easily detected by Southern blot hybridization and PCR tests can also determine the genetic purity of the vaccine virus from the wild type. Therefore, what is needed is an avirulent gE-deleted IBRV strain which contains a suitable phenotypic/histochemical/genotypic β-gal marker.

SUMMARY OF THE INVENTION

A BHV-1 recombinant virus (gEΔ3.1IBRβ) has been constructed in which gE open reading frames (ORF's) comprising a portion of the gE gene-coding sequences have been deleted and a chimeric reporter/marker gene has been inserted in their place. The inserted β-galactosidase (β-gal) gene plays no regulatory role in the replication of the virus but does serve as a phenotypic marker for gEΔ3.1IBRβ virus.

To construct this recombinant BHV-1, the BHV-1 gE gene-coding region and the flanking upstream and downstream sequences were cloned. To create a deletion in the gE gene-coding region, the above cloned DNA was digested with suitable enzymes to release the amino two-thirds of that region and ligated to the β-gal gene. The resulting plasmid DNA was cotransfected with DNA from full-length, wild type IBR virus strain Cooper into MDBK cells. Recombinant viruses expressing β-gal (blue plaques) were plaque purified and assayed further by blot hybridization for genetic characterization and by immunoblotting for reactivity against BHV-1 gE peptidespecific rabbit polyclonal antibody. One recombinant virus, gEΔ3.1IBRβ, was characterized in vitro for its growth properties and in vivo in calves for its pathogenic properties. The ability of the recombinant virus to induce BHV-1 neutralizing antibodies in infected calves was investigated by plaque reduction tests.

The regulation and expression of the chimeric β-gal gene are unique to this recombinant BHV-1 virus in two ways. The first unique aspect of this recombinant virus is that the β-gal gene is regulated by a strong human cytomegalovirus immediate early (HCMV-IE) promoter (not by a BHV-1-derived regulatory sequence). The second unique aspect is that the gene is expressed as a BHV-1-encoded gene at both early and late phases of infection. The in vitro and in vivo properties of this gE-deleted recombinant virus were analyzed by comparing it with the parental IBRV strain Cooper.

In tissue culture experiments, gEΔ3.1IBRβ virus grew to a lower titer than the wild type (parent strain Cooper) at early times post-infection, but at late times postinfection, the recombinant virus grew to an almost equal titer to the wild type strain. The recombinant virus usually developed significantly smaller plaques compared to the parental wild type strain Cooper. This could have been due to the lack of cell-to-cell spread of virus and is consistent with the results for other herpesviruses.

In animal experiments, gEΔ3.1IBRβ-infected calves shed approximately 100-fold less virus compared to the parental strain Cooper infected calves throughout the duration of virus shedding. The duration of this virus shedding was also two days shorter for calves infected by gEΔ3.1IBRβ. Whereas the calves infected with gEΔ3.1IBRβ virus remained healthy, the calves infected with parental strain Cooper showed typical IBR symptoms and lesions. Results of serum neutralization indicated that both the wild type and gE-deleted IBRV infected calves induced comparable BHV1 neutralizing antibody. It has been previously reported that thymidine kinase (TK) gene-deleted IBRV grew, both in vitro and in vivo, with a significantly lower titer (Chowdhury, S. I., Construction and Characterization of an Attenuated Bovine Herpesvirus Type 1 (BHV-1) Recombinant Virus, 52 Vet. Microbiol. 13–23 (1996)). Taken together, these results indicate that even though the recombinant gEΔ3.1IBRβ virus grows relatively well compared with the TK-deleted IBR, the gEΔ3.1IBRβ virus was virtually avirulent for the calves. The attenuated properties exhibited by the recombinant gEΔ3.1IBRβ virus paralleled those exhibited by: 1) deletion of TK in BHV-1 as shown by Chowdhury, S. I., in Construction and Characterization of an Attenuated Bovine Herpesvirus Type 1 (BHV-1) Recombinant Virus (52 Vet. Microbiol. 13–23 (1996); 2) deletion of gE in PRV as shown by Kritas et al., in, Invasion and Spread of Single Glycoprotein Deleted Mutants of Aujeszky's Disease Virus (AD V) in the Trigeminal Nervous Pathway of Pigs After Intranasal Inoculation (50 Vet. Micobiol. 323–334 (1994)) and Kritas et al., in, Role of Envelope Glycoproteins gI, gp63 and gIII in the Invasion and Spread of Aujeszky 's Disease Virus in the Olfactory Nervous Pathway of the Pig (75 J. General Virol. 2319–2327 (1994)); and 3) European gE-deleted IBRV vaccine isolate as shown by Kaashoek et al., in, An Inactivated Vaccine Based on a Glycoprotein E-Negative Strain of Bovine Herpesvirus 1 Induces Prospective Immunity and Allows Serological Differentiation (13 Vaccine 342–346 (1995)) and Van Englenburg et al., in, A Glycoprotein E Deletion Mutant of Bovine Herpesvirus 1 Infects the Same Limited Number of Tissues in Calves as Wild-Type Virus, butfor a Shorter Period (76 J. Gen. Virol. 2387–2392 (1994)).

This study also demonstrated that the deletion of the gE ORF sequences and the insertion of a functional β-gal gene at the gE locus of the virus stably attenuated the virus. A practical application of this virus is its use as a safe live vaccine directed against IBR. The deletion of the gE gene will serve as an immunological marker to differentiate the vaccinated animals from the infected animals. In addition, production of β-gal would permit easy assessment of gEΔ3.1 IBRβ virus replication in the nasal epithelium of vaccinated animals in comparison to the current gE-deleted vaccine strain in Europe which lacks this phenotypic β-gal marker, as well as distinguishing it from infection caused by wild type IBR virus.

DETAILED DESCRIPTION OF THE PREFERRED EMBODIMENT

The following examples describe the construction of an infectious recombinant BHV-1 having a deleted native gE coding region thereby attenuating the virus and having a functional β-gal gene inserted at the gE locus, a method of immunizing animals against diseases caused by BHV-1 using this recombinant BHV-1 as a vaccine, and methods of detecting and differentiating infection by this recombinant virus and the wild type virus in an animal both genotypically and phenotypically. These examples are set forth by way of illustration only, and nothing therein should be taken as a limitation upon the overall scope of the invention.

EXAMPLE 1

Materials and Methods

This experiment generated and characterized gE gene-deleted and β-galactosidase-expressing recombinant IBRV. The recombinant virus constructed contains a chimeric gene (4.5 Kb long) which replaced the gE coding region of BHV-1. The chimeric gene is preferably composed of a HCMV-IE promoter and its enhancer sequences linked to β-gal gene coding sequences which are linked to $SV_{40}$ polyadenylation sites. Preferably, the β-gal coding sequences are bacterial, however, it is believed that any β-gal gene coding sequences will work.

To construct and characterize the recombinant BHV-1 the Cooper (Colorado-1) strain of IBRV was obtained from the American Type Culture Collection. Viruses were propagated and titrated in Madin-Darby bovine kidney cells using the method of Chowdhury S. I., Molecular Basis ofAntigenic Variation Between Glycoprotein C (gC) of Respiratory Bovine Herpesvirus 1 (BHV-1) and Neurovirulent BHV-5, 213 Virology 558–568 (1995), the method of which is hereby incorporated by reference. The viral DNA was isolated using sodium dodecylsulfate and protein K lysis, phenol/chloroform extraction, and ethanol precipitation as described in Chowdhury et al., Equine Herpesvirus Type 1 (EHV-1) Induced Abortions and Paralysis in a Lipizzaner Stud: A Contribution to the Classification of Equine Herpesviruses, 90 Arch. Virol. 273–288 (1986), the method of which is hereby incorporated by reference.

BHV-1 gE-specific anti-peptide rabbit polyclonal serum was synthesized based on predicted regional hydropathicity and antigenicity. This gE peptide containing residues 378–398 as described by Leung—Taek, P. et al., The Complete DNA Sequence and the Genetic Organization of the Short Unique Region ($U_S$) of the Bovine Herpesvirus Type 1 Strain (ST strain), 199 Virology 409–421 (1994) was synthesized, the sequence and genetic organization of which is hereby incorporated by reference. The 9-fluorenyl-methoxycarbonyl (FMOC) chemistry as described in Abdelmagid et al., Fine Mapping of Bovine Herpesvirus-1 (BHV-1) Glycoprotein D (gD) Neutralizing Epitopes by Type-Specific Monoclonal Antibodies and Sequence Comparison With BHV-5 gD, 206 Virology 242–253 (1995), was used to perform the synthesis of the gE peptide, the method of which is hereby incorporated by reference. To facilitate conjugation to keyhole limpet hemocyanin (KLH), an additional irrelevant cysteine (C) (marked with a *) was added at the C-terminus of the peptide. The 17 mer peptide [H]-TSDRLVRAVTDHTRPEC*-[OH] (SEQ ID NO; 1) was coupled to KLH, and antisera were prepared as described in Kyte, J., Doolittle, R. F., A Simple Method for Displaying the Hydropathic Character of Protein, 157 J. Mol. Biol. 105–132 (1982), the method of which is hereby incorporated by reference.

SDS-PAGE and Western blot of mock and virus infected cell proteins were performed under reducing conditions as described in Chowdhury S. I., Molecular Basis of Antigenic Variation Between Glycoprotein C (gC) of Respiratory Bovine Herpesvirus 1 (BHV-1) and Neurovirulent BHV-5, 213 Virology 558–568 (1995) and Laemli, U. K., Cleavage of Structural Proteins During the Assembly of the Head of Bacteriophage T4, 227 Nature (London) 680–685 (1970), the methods of which are hereby incorporated by reference.

The construction of recombinant plasmids was accomplished by obtaining plasmids pBHV1HK and pBHV1HF from Dr. W. Lawrence (U. Pennsylvania, Philadelphia, USA). Respectively, the plasmids contained the HindIII-K and HindIII-F fragments of BHV-1 DNA. A 4.4 Kb XhoI/HindIII subfragment from plasmid pBHV1HK containing the entire gD gI, and a portion, preferably the amino terminal two-thirds of the gE-coding region was subcloned into the XhoI/HindlII sites of plasmid pGEM7Z (pBHV1gE5'). Next a 1.15 Kb HindIII/Bsu36I (blunt ended by Klenow) fragment from pBHV1HF containing the carboxy terminal third of the gE-coding region and the entire US9 ORF coding sequence was subcloned into the HindIII/HincII sites of plasmid pBluescript KS (pBHV1gE3'). Finally, to assemble the entire gE gene coding region and its flanking sequences, the 4.4 Kb HindIII/XbaI vector site fragment of pBHV1gE5' containing the HindIII/XhoI fragment was cloned into the HindIII/XbaI sites of the plasmid pBHV1gE3'. The resulting clone was designated as pBHV1gE5'3'.

To delete the gE-coding region, the pBHV1gE5'3' DNA was partially digested with AsuII and subsequently redigested to completion with HindIII. The larger fragment was gel purified and ligated to the 4.5 Kb PstI fragment (blunt ended with T4 polymerase) of pCMVβ (obtained from Clontech, Palo Alto, Calif., USA), which contains the CMV early promoter-regulated β-gal sequences. The resulting gE-deletion/β-gal-insertion plasmid, pBHV1gEΔβ (ATCC Accession No. 203607), has a deletion of 1 Kb BHV-1 DNA sequences containing the gene sequences coding for the first 372 amino acids and an insertion of the β-gal gene under the regulation of the CMV promoter. The β-gal gene is flanked by virus specific 3.32 Kb upstream sequences (containing the entire gD and gI gene sequences and the gE-promoter sequences) and 1.15 Kb downstream sequences (containing the carboxy terminal third of the gE-coding region and the entire US9 gene sequences) which are required for the recombination with the virus DNA.

To generate gE-deleted IBR recombinant virus, linearized pBHV1gEΔβ (ATCC Accession No. VR-2637) and full length wild type IBRV (strain Cooper) DNA were cotransfected by lipofection in Madin-Darby bovine kidney (MDBK) cells. The correct insertion of β-gal at the gE locus in the full length IBRV and subsequent deletion of the portion of the wild type IBRV gE coding region is due to homologous recombination of the BHV-1 specific flanking sequences in the plasmid with the replication of virus DNA. The virus specific flanking sequence gets incorporated into newly synthesized viral DNA creating a deletion in the coding region as well as inserting in the same region. Recombinant viruses expressing β-gal were plaque purified three times by screening for blue plaques under a Bluo-Gal overlay as described in Chowdery, S. I., Construction and Characterization ofan Attenuated Bovine Herpesvirus Type 1 (BHV-1) Recombinant Virus, 52 Vet. Microbiol. 13–23 (1996), the method of which is hereby incorporated by reference. Several recombinant isolates were characterized further by blot hybridizations and by immunoblotting with anti-BHV-1 gE-specific anti-peptide rabbit polyclonal serum. The blot hybridization method of Chowdery, S. I., Construction and Characterization ofanAttenuatedBovine Herpesvirus Type 1 (BHV-1) Recombinant Virus, 52 Vet. Microbiol. 13–23 (1996) was used and is hereby incorporated by reference. The immunoblotting method of Chowdhury S. I., Molecular Basis of Antigenic Variation Between Glycoprotein C (gC) of Respiratory Bovine Herpesvirus 1 (BHV-1) and Neurovirulent BHV-5, 213 Virology 558–568 (1995) was used and is hereby incorporated by reference.

Results

Figure 1:
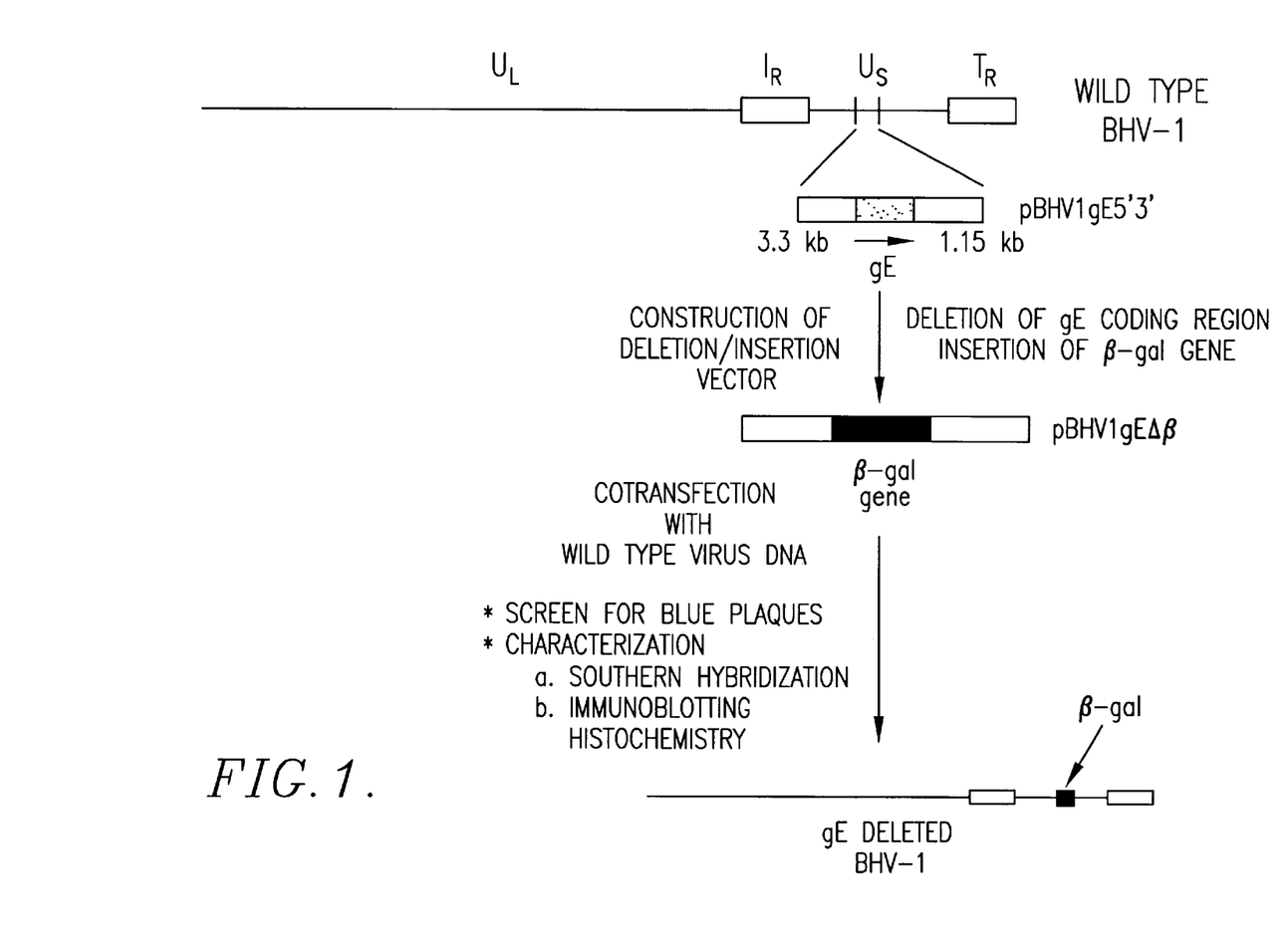
FIG. 1 is a flow diagram outlining the construction of gE-deleted BHV-1 virus (gEΔ3.1IBRβ), and an insertion/deletion vector plasmid containing a functional β-gal gene replacing the amino terminal two-thirds of the gE coding region.
Figure 2:
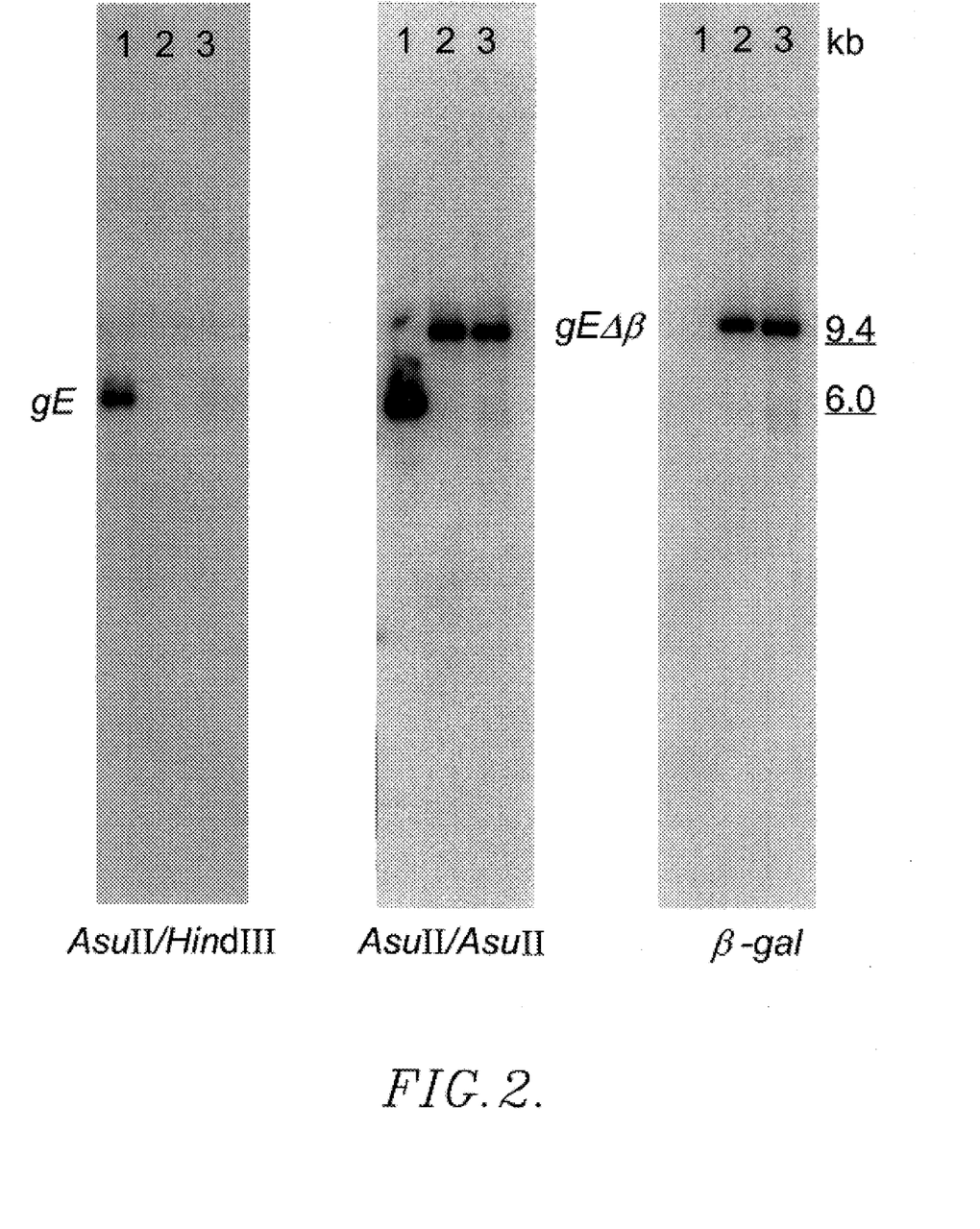
FIG. 2 is a reproduction of the Southern blot hybridization for the intended deletion of the gE coding region and the insertion of β-gal sequences at the gE locus.
Figure 3:
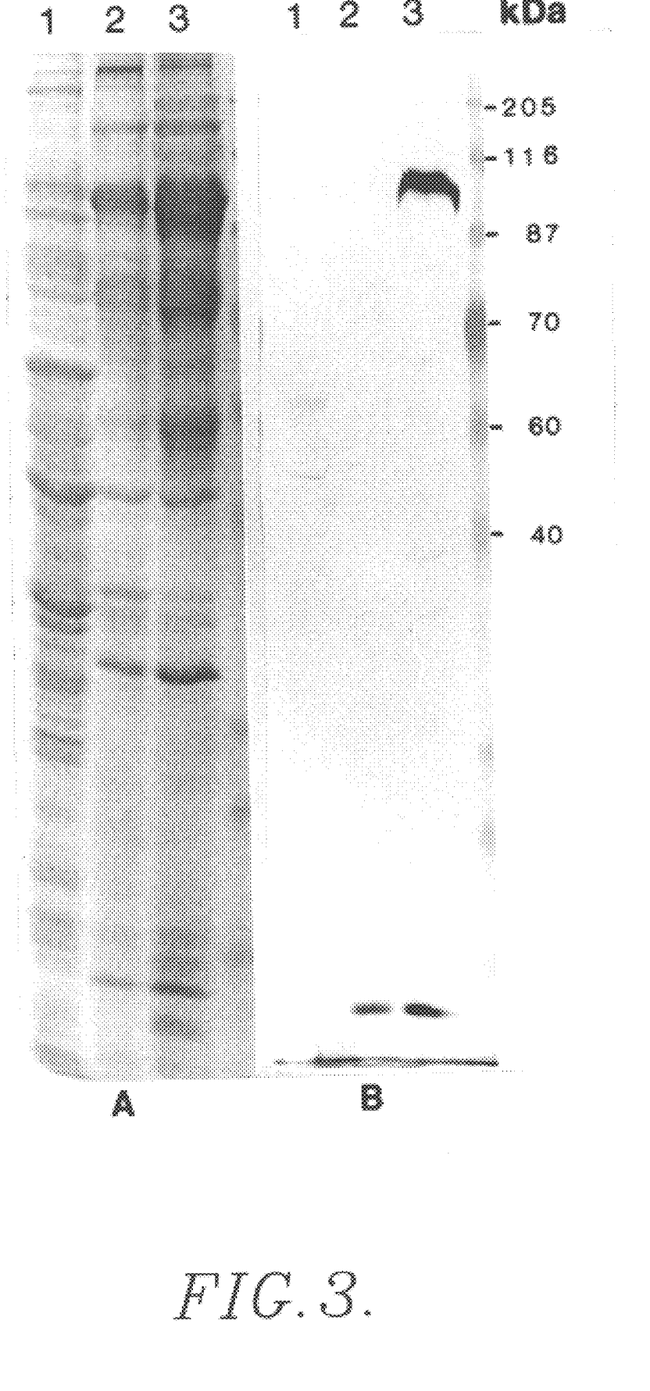
FIG. 3 shows the BHV-1 gE protein detected in the wild type parental Cooper strain but not detected in the gE-deleted recombinant virus (gEΔ3.1IBRβ)

Analysis of DNA from two recombinant viruses, gEΔ3.1IBRβ (ATCC Accession No. VR-2637) and gEΔ3.5IBRβ, by Southern blot hybridization for the intended deletion and the insertion of β-gal sequences at the gE locus is shown in FIG. 2. The absence of the 1 Kb AsuII-HindIII fragment sequences coding for the first 372 amino acids at the amino terminal end of the gE gene and the presence of β-gal sequences in isolates gEΔ3.1IBRβ and gEΔ3.5IBRβ demonstrated that the intended recombination had taken place in a site-specific manner in these isolates. Consistent with this finding, the 92–95 Kd BHV-1 gE protein was detected in the wild type parental Cooper strain by the BHV-1gE specific anti-peptide rabbit polyclonal serum but was lacking in the gE-deleted recombinant virus gEΔ3.1IBRβ. This result is shown in FIG. 3 and that isolate was used for further studies. Additionally, gEΔ3.1IBRβ could be reverted back to wild type IBR by cotransfecting with the plasmid containing the flanking sequences and original gE sequence from a wild type IBRV. This essentially reverses the cotransfection process used to generate gEΔ3.1IBRβ.

The kinetics of -gal expression in virus infected MDBK cells were determined histochemically, at 3, 6, 12 and 24 hours post-infection. β-gal activity was detected as early as three hours and as late as 24 hours post-infection. This demonstrates that the CMV-IE promoter-regulated β-galactosidase gene of the gEΔ3.1IBRβ virus is expressed at both early and late times. Furthermore, even though the chimeric gene is regulated by a foreign human herpesvirus HCMV-IE promoter and contains nonviral β-gal sequences as well as enhancers that are foreign to both β-gal and BHV-1, it is regulated and expressed as an authentic BHV-1 gene. Therefore, the β-gal is foreign (not present in BHV-1's natural state) to BHV-1 and the HCMV-IE and its enhancer sequences are foreign to both BHV-1 and the β-gal that they regulate/enhance.

Deletion of the gE gene will serve as an immunological marker to differentiate the vaccinated animals from the infected animals. Antibody response induced by vaccine strain would lack gE specific antibody which can be differentiated from the response induced by wild type BHV-1 infection which would contain gE specific antibody. Thus infected animals in a vaccinated herd can be identified and culled. This serological marker is important for the elimination of BHV-1 from the herd.

The plasmid (pBHV1gEΔβ) used to generate the recombinant virus and the generated recombinant virus, gEΔ3.1IBRβ, have been deposited with the American Type Culture Collection (ATCC). The plasmid (pBHV1gEΔβ) has been assigned ATCC Accession No. 203607 and the recombinant virus (gEΔ3.1IBRβ) has been assigned ATCC Accession No. VR-2637.

EXAMPLE 2

Materials and Methods

This experiment determined the pathogenicity of gEΔ3.1IBRβ virus in calves and compared these results to the pathogenicity of parental Cooper strain IBRV. Ten 6-month old Holstein calves free of IBRV and bovine viral diarrhoea virus were divided randomly into two groups (A and B) of five calves each. The two groups were housed in isolation stables under identical conditions. Prior to the experiment, all calves were healthy and remained seronegative until the start of the experiment.

Each calf in group A was inoculated intranasally with the recombinant gE-deleted IBRV. Each calf in group B was inoculated intranasally with the parental Cooper strain IBRV. The inocula contained $1 \times 10^7$ TCID$_{50}$ of the respective virus per animal. All inoculation was done by aerosolization using a DEVILBIS model 50 nebulizer from Delvis Co., Somerset, Pennsylvania, with 2 ml of inocula per nostril over a period of 30 seconds to one minute.

Intensive clinical observation of all calves was performed daily for 14 days following virus exposure (inoculation). Rectal temperatures were recorded daily. Special attention was given to the following conditions: behavior (depression), appetite, cough, ocular and nasal discharges, hyperemia or lesions of the nasal and oral mucosae, conjunctivitis, and abnormal breathing. Each condition was individually scored and daily clinical scores for each calf as well as the mean daily clinical scores for each group were computed by adding up all of the scores for each condition. Scoring parameters were as follows:

| | |
|---|---|
| Nasal Discharge | Normal = 0; Moderately Serous = 1; Severely Serous = 2; Mildly Micropurulent = 2; Moderately Micropurulent = 3; and Severely Micropurulent = 4 |
| Behavior (Depression) | Not Present = 0; Mild = 1; Moderate = 2; Severe = 3 |
| Hyperimia/Reddening of Nasal Mucosa = 1 | |
| Ulcers of Nasal Mucosa = 2 | |
| Conjunctivitis = 2 | |
| Coughing = 2 | |
| Dyspnea = 2 | |
| Daily Rectal Temperature | 39.7–39.99° C. = 1; 40.0–40.5° C. = 2; 40.6–41.0° C. =3; above 41.0° C. = 4 |

Results

Figure 5:
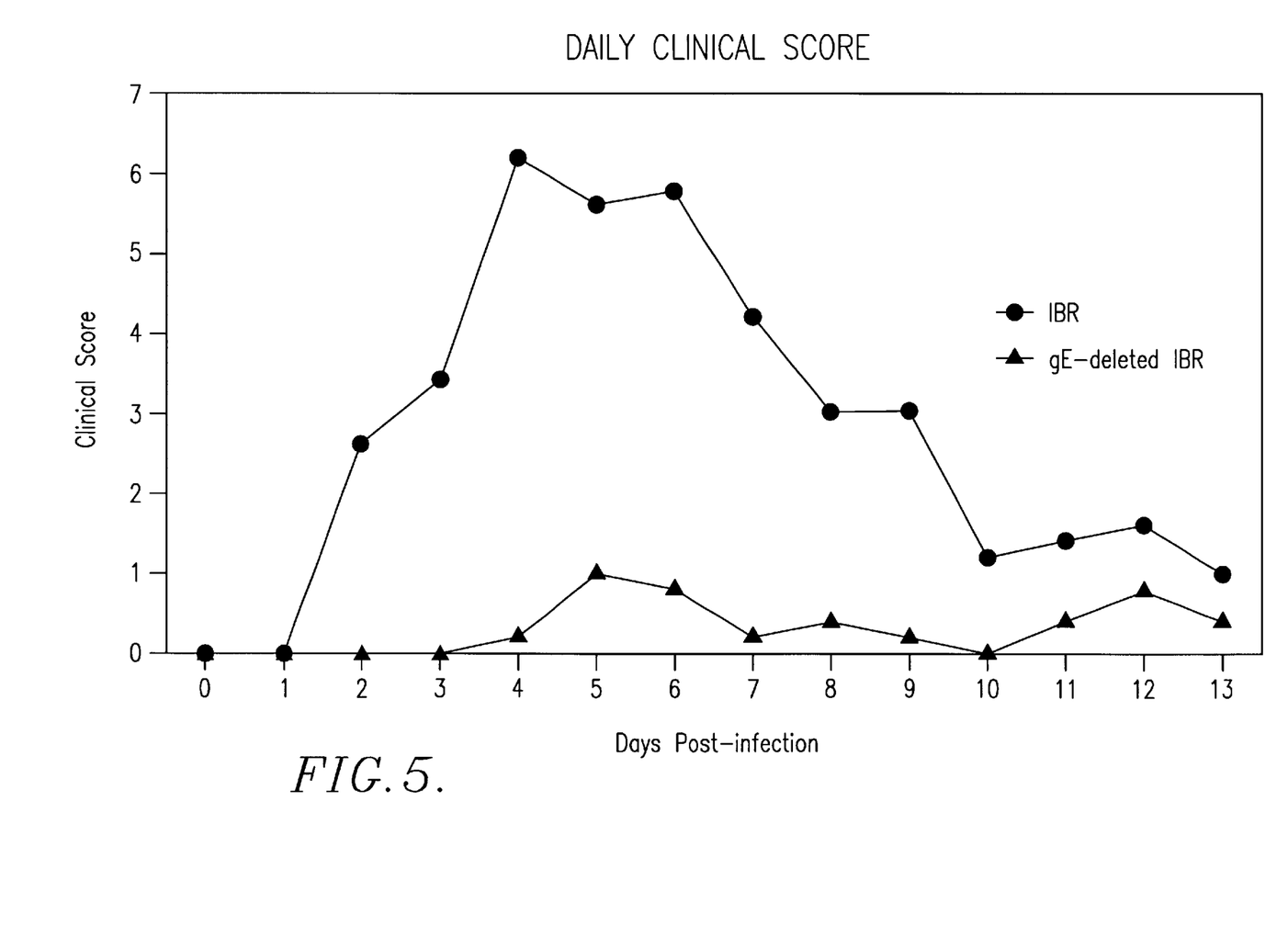
FIG. 5 is a graph comparing the daily clinical scores of calves infected with gE-deleted IBR with the daily clinical scores of calves infected with wild type IBR, with each data point representing the average of results obtained from each group of calves.
Figure 6:
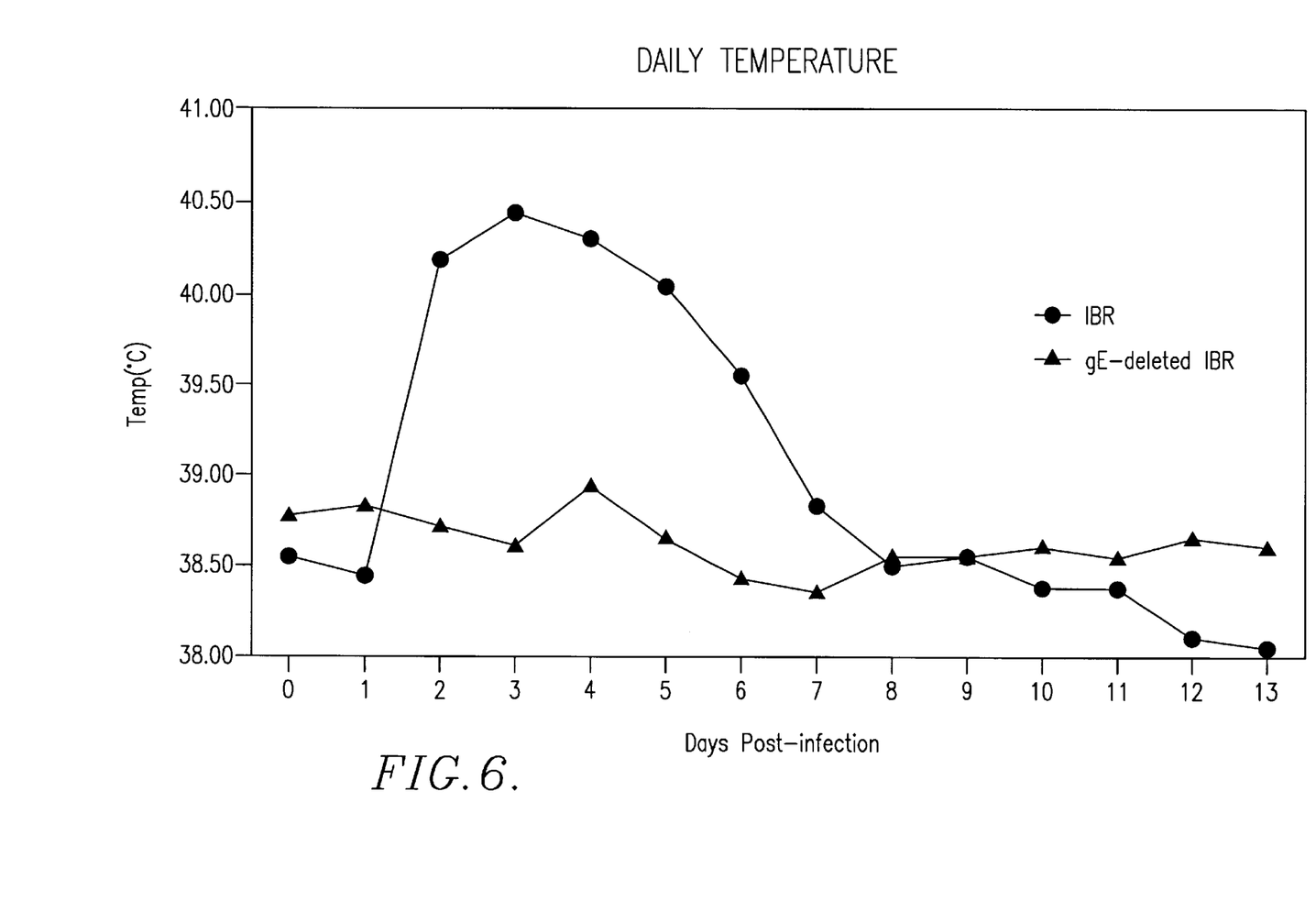
FIG. 6 is a graph comparing the daily rectal temperatures of calves infected with gE-deleted IBR with the daily rectal temperatures of calves infected with wild type IBR with each data point representing the average of results obtained from each group of calves.

Calves in group B infected with the parental Cooper strain of IBRV (wild type IBRV) showed typical signs of infection: depression, reduced appetite, ocular and nasal discharges, nasal ulcers/nasal plaques, and coughing. These clinical findings resulted in a high daily clinical score over several days as shown in FIG. 5. However, the calves infected with the recombinant gEΔ3.1IBRβ virus (group A) did not exhibit any detectable clinical signs (also shown in FIG. 5) and their behavior and appetite remained normal. FIG. 6 compares the mean rectal temperatures of the calves from each group (A and B). High rectal temperatures from 39.7° C.–40.5° C. were recorded over several days for calves infected with parental strain Cooper (group B). Rectal temperatures greater than 38.9° C. were never recorded for the calves infected with gEΔ3.1IBRβ (group A).

EXAMPLE 3

Materials and Methods

This experiment compared the kinetics of growth between gEΔ3.1IBRβ virus in MDBK cells and parental IBR strain Cooper in MDBK cells. A series of replicate cultures of MDBK cells were infected separately with 5 plaque forming units (PFU)/cell of either recombinant gEΔ3.1IBRβ or parental strain Cooper. Infected cultures were harvested at successive intervals post-infection, and virus stocks were prepared for use in virus titration assays.

Results

Figure 4:
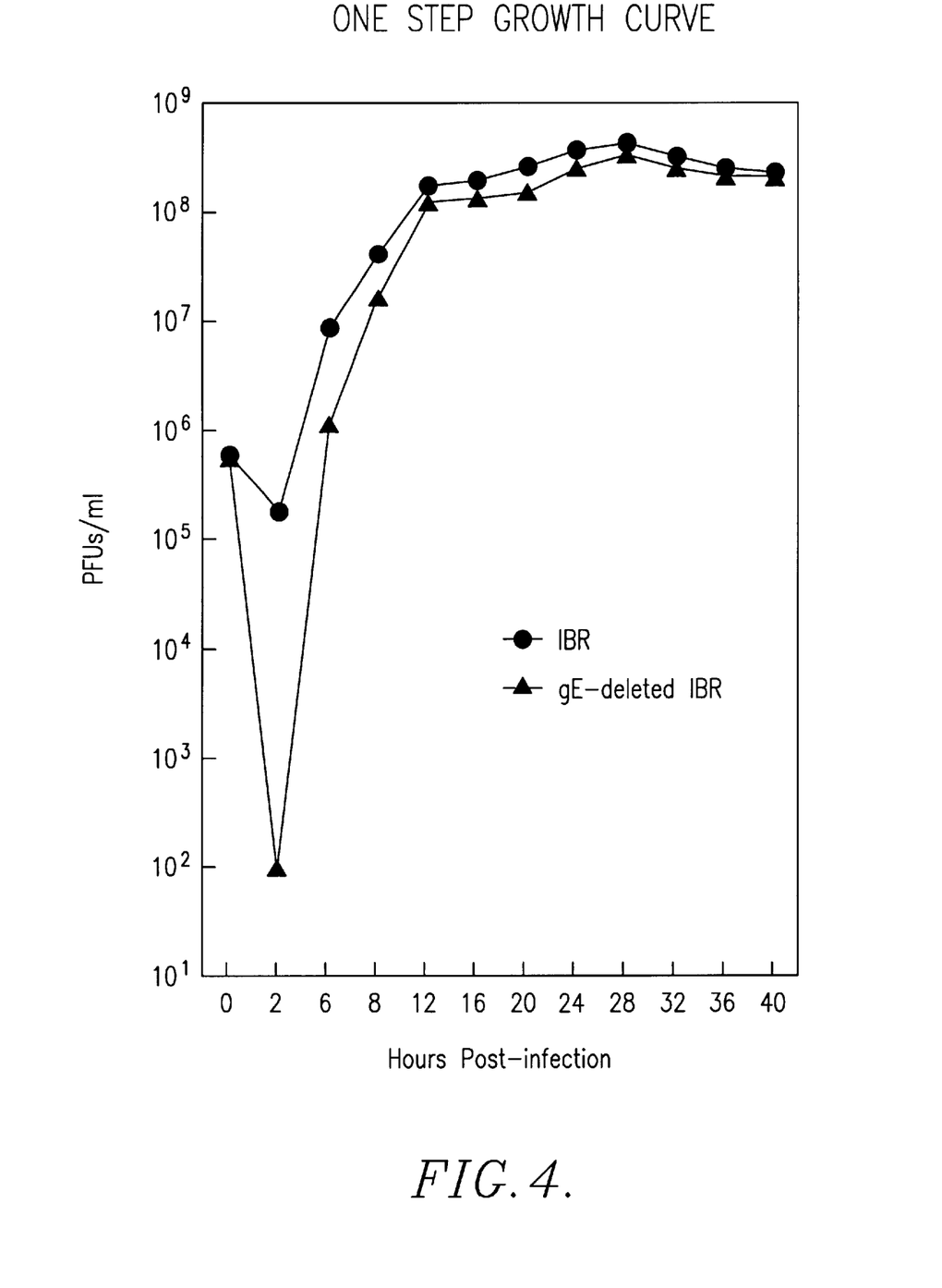
FIG. 4 is a graph illustrating the result of the one-step growth experiment comparing the gE-deleted IBR growth rate with the wild type IBR growth rate in MDBK cells, with each data point representing the average of results obtained from each group of calves.

Results of the one-step growth experiment are shown in FIG. 4. The virus growth curves demonstrate that the time courses of progeny viruses were similar between gEΔ3.1IBRβ and the parental strain Cooper. However, the recombinant virus yielded less at early times post infection.

EXAMPLE 4

Materials and Methods

This experiment isolated and quantitated the virus from each animal in groups A and B (from example 3 above). A plain cotton tip swab was inserted into each nasal cavity. The swab was rotated three times against the mucosae. Virus was eluted from the swab in 3 ml of sample medium (MEM containing 100 μg/ml Gentamycin, 3% v/v FBS, Amphotericin B at 25 μg/ml) for one hour at room temperature. Samples were clarified by centrifugation at 1000 g for five minutes and stored at −70° C. Virus isolation in MDBK cells was carried out using 100 μl of 1:10 diluted swab suspension.

Virus positive samples were titrated on microtiter plates. Serial tenfold dilutions were made in culture medium, and 50 μl of each dilution was added to each of eight wells (in a 96 well plate) containing $1.5 \times 10^5$ MDBK cells. After 5 days at 37° C., plates were read microscopically for cytopathic effect (CPE). Virus titers were calculated in TCID$_{50}$ according to the method of Reed, L. J., and Muench, H., 27 Am. J. Hyg. 493 (1938), the method of which is hereby incorporated by reference.

Results

Figure 7:
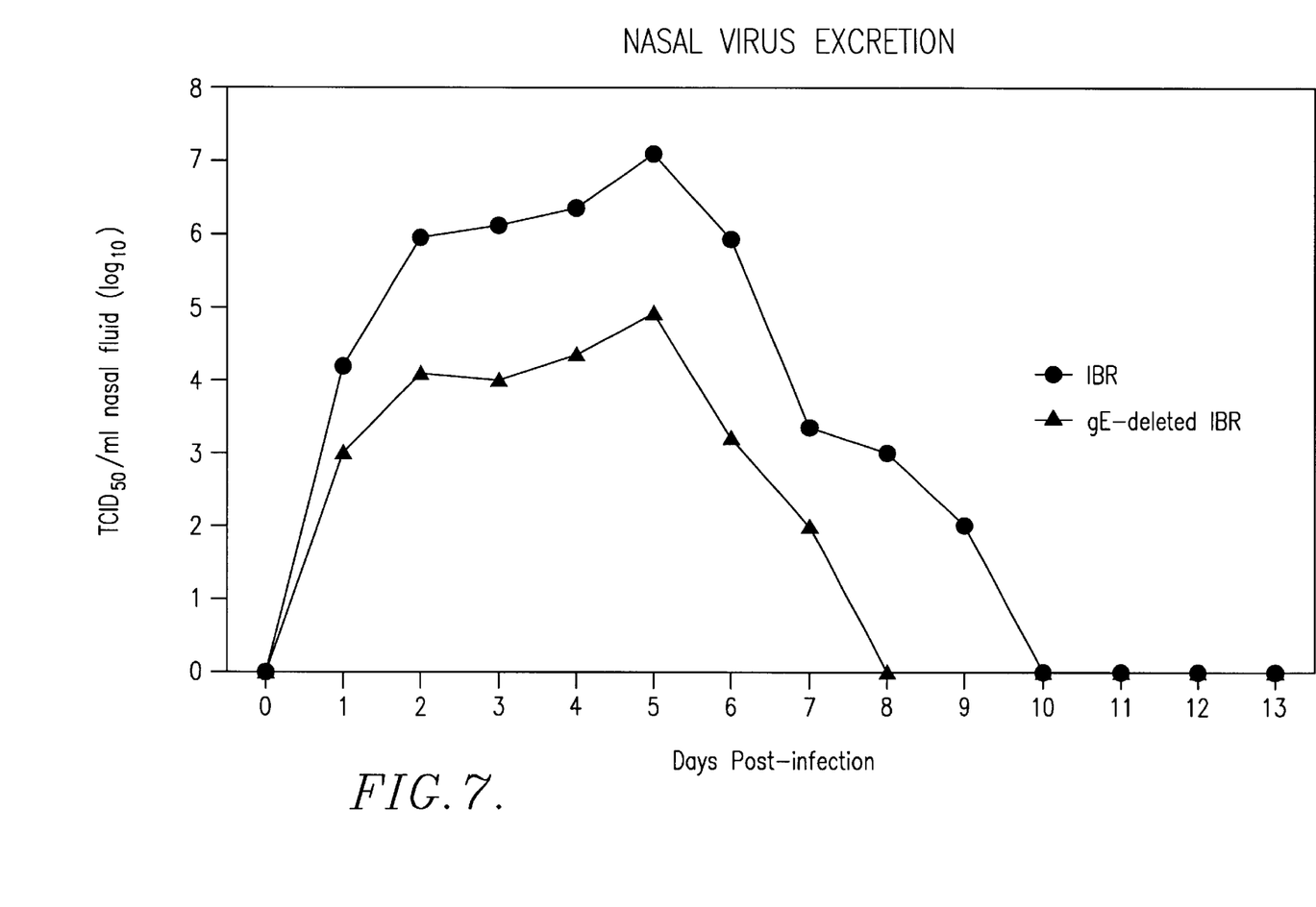
FIG. 7 is a graph comparing nasal virus excretion of gE-deleted IBR with nasal virus excretion of wild type IBR with each data point representing the average of results obtained from each group of calves.

The amount of virus isolated from nasal swabs demonstrated that the gEΔ3.1IBRβ virus grew less efficiently in the nasal epithelial cells compared to its parental strain Cooper. Shedding of virus in nasal secretions is shown in FIG. 7.

This virus shedding was approximately 15 to 550-fold lower for gEΔ3.1IBRβ virus than for the wild type BHV-1 (parental strain Cooper). The duration of virus shedding was also 2 days shorter for gEΔ3.1IBRβ infected calves than for the calves infected with the wild type virus.

EXAMPLE 5

Materials and Methods

This example determined the titers of BHV-1 neutralizing antibodies in serum taken from the calves in groups A and B (from examples 3 and 4 above). Blood samples were collected at 13 days post infection from each calf from both groups A and B. BHV-1 neutralizing antibody titers in the serum were determined by plaque reduction method using 12 well plates as described in Chowdhury, S. I., et al., Molecular Biological Characterization of Equine Herpesvirus 1 (EHV-1) Isolated From Ruminant Hosts, 11 Virus Res. 127–139 (1988), the method of which is hereby incorporated by reference.

Results

Both the wild type (parental strain Cooper) and gE-deleted IBRV viruses (gEΔ3.1IBRβ) induced BHV-1 neutralizing antibody in calves. However, sera of calves infected with the wild type had slightly higher neutralizing titers (1:20–1:35 with a mean titer of 1:30) when compared to the gE-deleted antibody titers (1:11–1:30 with a mean titer of 1:16).

I claim:

1. An attenuated recombinant bovine herpesvirus type I virus comprising a bovine herpesvirus type I having a portion of a native coding region thereof deleted and replaced with a genetic insert, said portion being deleted only from the glycoprotein E coding region, said insert comprising the coding region of a foreign β-galactosidase gene and including human cytomegalovirus immediate early promoter, said recombinant virus expressing β-galactosidase in a host cell.

2. The virus of claim 1, said insert further comprising enhancer sequences of said human cytomegalovirus immediate early promoter.

3. The virus of claim 1, said deleted portion comprising about two-thirds of said native glycoprotein E coding region.

4. The virus of claim 2, said insert being linked to $SV_{40}$ polyadenylation sites.

5. The virus of claim 1, said foreign β-galactosidase gene being expressed as an authentic bovine herpesvirus type I encoded gene.

6. The virus of claim 1, said deleted native coding region serving as a genotypic marker.

7. The virus of claim 1, said genetic insert serving as a phenotypic marker.

8. The virus of claim 1, said deleted native coding region serving as an immunological marker.

9. The virus of claim 1, said β-galactosidase coding sequences being expressed in said host cell at both early and late stages of infection.

10. The attenuated virus of claim 1, said virus capable of normal replication in vitro and substantially normal replication in vivo.

11. The attenuated virus of claim 1, said deleted portion being responsible for attenuation.

12. A vaccine effective in inducing bovine herpesvirus type I neutralizing antibodies comprising the recombinant virus of claim 1.

13. The vaccine of claim 12, said deleted portion comprising two-thirds of said native glycoprotein E coding region.

14. The vaccine of claim 13, said insert comprising human cytomegalovirus immediate early promoter and enhancer sequences of said human cytomegalovirus immediate early promoter.

15. The vaccine of claim 12, said insert being linked to $SV_{40}$ polyadenylation sites.

16. The vaccine of claim 12, said β-galactosidase gene being expressed as an authentic bovine herpesvirus type I encoded gene.

17. The vaccine of claim 12, said β-galactosidase coding sequences being expressed in said host cell at both early and late stages of infection.

18. The vaccine of claim 12, said deleted native glycoprotein E coding region serving as a genotypic marker.

19. The vaccine of claim 12, said inserted β-galactosidase coding sequences serving as a phenotypic marker.

20. The vaccine of claim 12, said deleted native coding region serving as an immunological marker.

21. A method of immunizing cattle against bovine herpesvirus type I comprising inoculating said cattle with the recombinant virus vaccine of claim 12.

22. A method for identifying animals infected with recombinant virus vaccine of claim 12 comprising the steps of:

(a) obtaining a fluid sample containing said virus from an animal;

(b) infecting cells with said virus from said fluid sample; and (c) detecting said virus from the vaccine of claim 12 in said infected cells.

23. The method of claim 22, step (c) including analyzing for the presence of β-galactosidase.

24. The method of claim 22, step (c) step including analyzing for antibody response specific to glycoprotein E.

25.The method of claim 22, further including the step of identifying infected animals based on the presence or absence of antibody response specific to glycoprotein E.

26. The method of claim 22, step (c) including in situ histochemical methods for the detection of β-galactosidase enzyine activity.

27. The method of claim 22, step (c) including in situ immuno-histochemical methods for the detection of β-galactosidase protein.

28. The method of claim 22, step (c) including immunoblotting for the detection of β-galactosidase protein.

29. The method of claim 22, step (c) including in situ histochemical methods for the detection of glycoprotein E.

30. A recombinant virus having ATCC Accession No. VR-2637.

31. A plasmid having ATCC Accession No. 203607.

* * * * *